United States Patent [19]

Duxbury

[11] 4,144,762
[45] Mar. 20, 1979

[54] ANALYZING PLASTIC CONCRETE

[76] Inventor: William G. Duxbury, 64 Winslade Rd., Sidmouth, Devon, England

[21] Appl. No.: 806,268

[22] Filed: Jun. 13, 1977

[51] Int. Cl.² ............................................. G01N 5/00
[52] U.S. Cl. .................................................... 73/432 R
[58] Field of Search ............... 73/432 R, 432 PS, 61.4

[56] References Cited

U.S. PATENT DOCUMENTS

| | | | |
|---|---|---|---|
| 2,264,223 | 11/1941 | Stancliffe | 73/432 PS UX |
| 3,419,139 | 12/1968 | Agthe | 73/432 PS X |
| 3,499,328 | 3/1970 | Kenny et al. | 73/432 R |
| 3,686,959 | 8/1972 | Kruiger | 73/432 R |
| 3,690,183 | 9/1972 | Livingood | 73/432 PS |
| 3,813,947 | 6/1974 | Hinde | 73/432 PS |
| 3,943,754 | 3/1976 | Orr, Jr. | 73/432 PS X |

*Primary Examiner*—Richard C. Queisser
*Assistant Examiner*—Joseph W. Roskos
*Attorney, Agent, or Firm*—Haseltine, Lake & Waters

[57] ABSTRACT

A method of analyzing plastic concrete comprising the steps of measuring a known amount of a plastic concrete sample into an elutriator, removing cement from the sample by passing a known weight of water through the sample, weighing the water and cement and determining the weight of cement in the sample. The method can be extended to determine, inter alia, the weight of cement per unit volume of concrete, the weight of water per unit volume of concrete, the ratio of water to cement in the samples. Apparatus for carrying out the method is also disclosed.

12 Claims, 2 Drawing Figures

4,144,762

ANALYZING PLASTIC CONCRETE

BACKGROUND OF THE INVENTION

This invention relates to a method of analysing plastic concrete and to apparatus for use in the method.

SUMMARY OF THE INVENTION

According to one aspect of the invention there is provided a method of analysing plastic concrete comprising the steps of measuring a known amount of plastic concrete sample into a container, removing cement and cement-fine material from the sample by passing a known weight of liquid through said sample, weighing the liquid with the cement and cement-fine material and determining from the known and measured parameters the weight of cement and cement-fine material in the sample.

Preferably the container is an elutriator and the liquid is water.

The sample may be a known weight of concrete and the method may further comprise the step of measuring the volume of the sample and determining the weight of cement and cement-fine material per unit volume of concrete.

The sample may be a known weight of concrete and the method may further comprise the steps of measuring the volume of the sample and determining the weight of water in the sample from the said known and measured parameters and the weight of cement and cement-fine material.

The method according to the next preceding paragraph may include the steps of determining the ratio of water to cement and cement-fine material of the concrete.

The method according to the two next preceding paragraphs may also include the step of determining the weight of the aggregate in the sample by subtracting the sum of the weights of the cement and cement-fine material and the water from the weight of the sample. The method may also comprise the step of obtaining the ratio of the weight of the aggregate to the weight of the cement and cement-fine material in the sample.

The method may also comprise the step of determining the plastic density of the concrete from the weight and the volume of the sample.

According to another aspect of the invention there is provided apparatus for performing the method according to the first aspect of the invention.

DESCRIPTION OF THE DRAWINGS

The invention will now be described by way of example with reference to the accompanying drawing, in which.

DETAILED DESCRIPTION OF THE INVENTION

Figure 1:
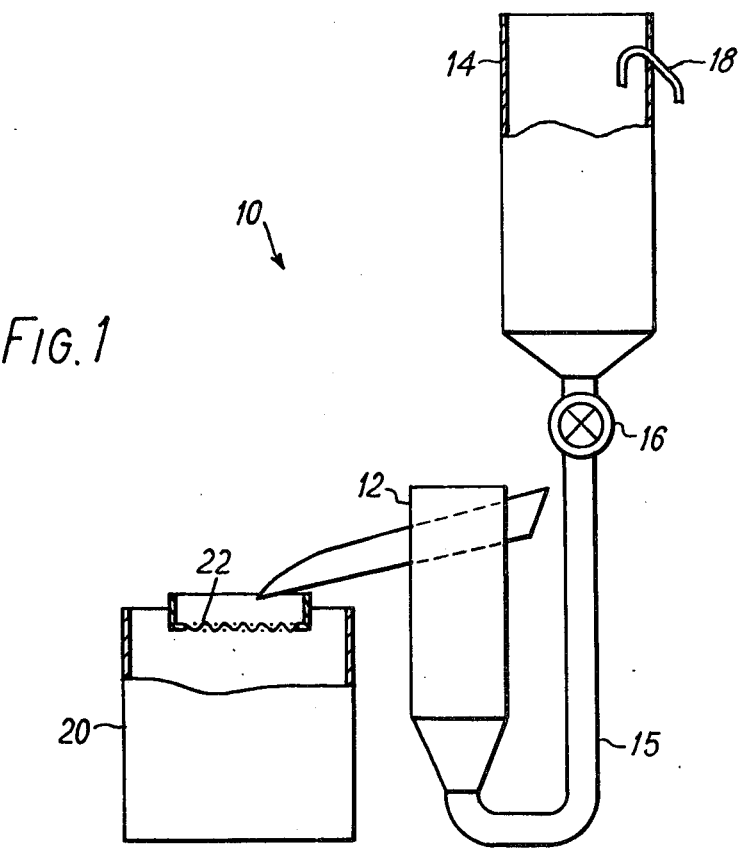
FIG. 1 is a schematic view of one apparatus for carrying out the method of testing concrete according to the invention.

Referring to FIG. 1 there is shown apparatus 10 for analysing plastic concrete. The apparatus 10 comprises an elutriator 12 supplied with water through a pipe 15 from a header tank 14, the supply being controlled by a valve 16. The outlet from the elutriator 12 is fed into a collection vessel 20. A sieve 22 at the inlet to the collection vessel 20 is arranged to collect any solid matter having a particle size greater than that of cement so that only cement and cement-fine material pass through.

Figure 2:
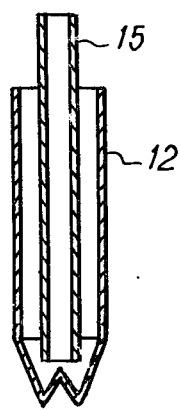
FIG. 2 shows an alternative arrangement of part of the apparatus of FIG. 1.

FIG. 2 shows another arrangement of the eutriator 12 and supply pipe 15 in which pipe 15 extends into the elutriator 12 with its open end positioned near to the bottom of the elutriator 12.

DETAILED DESCRIPTION OF THE INVENTION

In use, plastic concrete is analysed according to the following method:

(a) with valve 16 in the open position, the elutriator 12 is filled with water, any excess going to waste.

(b) with valve 16 in the closed position, water is poured into the header tank 14, until it begins to flow from the overflow siphons 18.

(c) when the overflow from the siphons 18 stops, the water in the header tank 14 is released by operation of valve 16 and allowed to flow down tube 15, through elutriator 12 and into the collection vessel 20, where it is weighed together with this vessel, to give weight W1.

(d) the water in collection vessel 20 is discarded and step (b) above repeated.

(e) a sample of 5 to 7 Kg of plastic concrete is weighed, weight = $W_S$.

(f) this sample is placed in the elutriator 12, and the water overflow collected in a measuring cylinder to indicate the volume V of concrete in the sample.

(g) the water is released from the header tank 14 by operation of valve 16 and flows down the tube 15 and through the elutriator 12, into the collection vessel 20, taking with it the cement and other material of cement fineness.

(h) any material retained on the sieve 22 is returned to the elutriator 12.

(j) the collection vessel 20 and its contents are re-weighed, weight $W_2$.

(k) if it is believed that cement still remains in the sample, then the contents of the collection vessel 20 are discarded, the processes in steps (b), (g), (h) and (j) are repeated, and any difference between $W_1$ and the new $W_2$ added to the original $W_2$.

(l) knowing the weight $W_S$ of the sample of conrete, the volume of the sample, V, the apparent specific gravity or the saturated-surface-dry specific gravity of the aggregate (2.65 in the example which follows), the specific gravity of cement (3.1 in the example), and the difference in weights of the collection vessel and contents, the weight of cement-fine material and some other constituents of the concrete can be calculated.

If the only information required is the cement content per cubic meter of concrete it is not necessary to weigh the concrete sample or to know the specific gravity of the aggregate.

The following example shows a typical example of the results of carrying out the method according to the invention and the method of calculating the various parameters.

LET: $W_1$ = initial weight of collection vessel and contents $W_2$ = final weight of collection vessel and contents
$W_S$ = weight of concrete sample
$W_C$ = weight of cement in concrete sample
$W_W$ = weight of water in concrete sample
$W_A$ = weight of aggregates in concrete sample
$V$ = volume of concrete sample $V_C$ = volume of cement in sample
$V_A$ = volume of aggregate in sample
$V_W$ = volume of water in sample (= $W_W$)
$S_C$ = specific gravity of cement = 3.1
$S_A$ = specific gravity of aggregate = 2.65 approx.
$S_W$ = specific gravity of water = 1

FORMULAE $$W_C = \frac{(W_2 - W_1) S_C}{S_C - S_W}$$

$$\therefore W_C = \frac{(W_2 - W_1) 3.1}{2.1}$$

$$W_W = \frac{(V - V_C) S_A - (W_S - W_C)}{S_A - S_W}$$

$$\therefore W_W = \frac{(V - V_C) 2.65 - (W_S - W_C)}{1.65}$$

$$W_A = W_S - (W_C + W_W)$$

cement/$m^3$ = $W_C \times 1000/V$
water/$m^3$ = $W_W \times 1000/V$
aggregate/$m^3$ = $W_A \times 1000/V$

EXAMPLE:

Let
 $W_1$ = 10,000 g
 $W_2$ = 10,420 g
 $W_S$ = 5,000 g
 $V$ = 2,080 ml
then $$W_C = \frac{(10420 - 100000) 3.1}{2.1} = 620 \text{ g}$$

$$W_W = \frac{(2080 - 620 \times \frac{1}{3.1}) 2.65 - 4380}{1.65} = 365 \text{ g}$$

$W_A$ = 5000 − (620 + 365) = 4015 g water/cement ratio = 365/620 = 0.59 aggregate/cement ratio = 4015/620 = 6.48 cement/$m^3$ = 620 × $\frac{1000}{2.080}$ = 297.6 kg water/$m^3$ = 365 × $\frac{1000}{2.080}$ = 175.5 kg aggregate/$m^3$ = 4015 × $\frac{1000}{2.080}$ = 1930 kg concrete/$m^3$ (plastic density)

= 5 × $\frac{1000}{2.080}$ = 2403.8 kg

Under normal circumstances, only $W_C$ would be required, followed perhaps by $W_W$, to obtain the water/cement ratio, but the other parameters are clearly easily determined.

The whole operation takes only a few minutes and can be carried out in virtually any location. The only skill required is in the calculations, but these are basic and can be predetermined and presented in graphical form, so that the operator has only to consult a chart instead or doing the calculations.

I claim:

1. A method of analyzing plastic concrete comprising the steps of: measuring a known amount of plastic concrete sample into a container, passing a known weight of liquid upwardly through said sample to remove cement and cement-fine material therefrom, weighing the liquid with the cement and cement-fine material and determining from the known and measured parameters the weight of cement and cement-fine material in the sample.

2. A method according to claim 1, in which the container is an elutriator and the liquid is water.

3. A method according to claim 1, in which the sample is a known weight of concrete and the method further comprises the step of measuring the volume of the sample and determining the weight of cement and cement-fine material per unit volume of concrete.

4. A method according to claim 1, in which the sample is a known weight of concrete and the method further comprises the steps of measuring the volume of the sample and determining the weight of water in the sample from the said known and measured parameters and the weight of cement and cement-fine material.

5. A method according to claim 4, including the steps of determining the ratio of water to cement and cement-fine material of the concrete.

6. A method according to claim 4, including the step of determining the weight of the aggregate in the sample by substracting the sum of the weights of the cement and the cement-fine material and the water from the weight of the sample.

7. A method according to claim 6, comprising the step of obtaining the ratio of the weight of the aggregate to the weight of the cement-fine material in the sample.

8. A method according to claim 3, comprising the step of determining the plastic density of the concrete from the weight and the volume of the sample.

9. Apparatus for analysing plastic concrete comprising an elutriator for containing a measured amount of a plastic concrete sample, means for passing a known weight of water through a sample in the container to remove cement and cement-fine material therefrom and means for weighing the water with the cement-fine material.

10. Apparatus according to claim 9, comprising means for measuring the volume of the sample and for determining the weight of cement and cement-fine material per unit volume of concrete.

11. Apparatus according to claim 9, further comprising means for measuring the volume of the sample and for determining the weight of water in the sample from the said known and measured parameters and the weight of cement-fine material.

12. Apparatus according to claim 11, comprising means for determing the weight of the agregate and the weight of the cement-fine material in the sample.

* * * * *